(12) United States Patent
Goerne et al.

(10) Patent No.: US 7,935,507 B2
(45) Date of Patent: May 3, 2011

(54) METHOD FOR TESTING SUBSTANCES ON BIOMATRICES

(75) Inventors: Martin Goerne, Hamburg (DE); Peter-Matthias Kaufmann, Wedemark (DE)

(73) Assignee: Humanautocell GmbH, Munich (DE)

( * ) Notice: Subject to any disclaimer, the term of this patent is extended or adjusted under 35 U.S.C. 154(b) by 526 days.

(21) Appl. No.: 11/721,174

(22) PCT Filed: Dec. 8, 2005

(86) PCT No.: PCT/EP2005/013178
§ 371 (c)(1),
(2), (4) Date: Jul. 30, 2008

(87) PCT Pub. No.: WO2006/061229
PCT Pub. Date: Jun. 15, 2006

(65) Prior Publication Data
US 2009/0130699 A1   May 21, 2009

(30) Foreign Application Priority Data
Dec. 8, 2004 (DE) .......... 10 2004 059 169

(51) Int. Cl.
*C12N 11/02* (2006.01)
(52) U.S. Cl. ........................................ 435/177
(58) Field of Classification Search .............. None
See application file for complete search history.

(56) References Cited

U.S. PATENT DOCUMENTS

| 6,103,255 | A * | 8/2000 | Levene et al. .......... 424/426 |
| 2002/0094514 | A1 | 7/2002 | Bowlin et al. |
| 2004/0063206 | A1 | 4/2004 | Rowley et al. |
| 2007/0166343 | A1 | 7/2007 | Goerne et al. |

FOREIGN PATENT DOCUMENTS

| WO | WO 98/44027 | 10/1998 |
| WO | WO 99/09149 | 2/1999 |
| WO | WO 01/87575 A2 | 11/2001 |

OTHER PUBLICATIONS

Kim et al. "Dynamic seeding and in vitro culture of hepatocytes in a flow perfusion system", Tissue Engineering, 2000, 6(1):39-48.*
Yoon et al. "Degradation behaviors of biodegradable macroporous scaffolds prepared by gas foaming of effervescent salts", J biomed Mater Res. 2001, 55:401-408.*
Qingpu Hou, et al., "Porous polymeric structures for tissue engineering prepared by a coagulation, compression moulding and salt leaching technique", Biomaterials, XP004412414, vol. 24, No. 11, May 2003, pp. 1937-1947.
Leatrese D. Harris, et al., "Open pore biodegradable matrices formed with gas foaming", Journal of Biomedical Materials Research, XP001021110, vol. 42, 1998, pp. 396-402.
Peter M. Kaufman, et al., Is there an Optimal Concentration of Cotransplanted Islets of Langerhans for Stimulation of Hepatocytes in Three Dimensional Matrices?, Transplantation, XP002369920, vol. 68, No. 2, Jul. 27, 1999, pp. 272-279.

* cited by examiner

*Primary Examiner* — Jon P Weber
*Assistant Examiner* — Bin Shen
(74) *Attorney, Agent, or Firm* — Oblon, Spivak, McClelland, Maier & Neustadt, L.L.P.

(57) ABSTRACT

The invention relates to a method for testing one or several substances. According to said method, a tissue equivalent is cultivated, the substance/s is/are made to affect the tissue equivalent, and it is determined whether the effect of the substance/s has resulted in a modification of the tissue equivalent and/or the substance/s. The tissue equivalent comprises at least one cell and a porous matrix based on a biologically compatible polymer or polymer mixture. The matrix is provided with pores having a maximum size of 150 μm as well as pores having a minimum size of 300 μm while the degree of porosity is 93 to 98 percent.

25 Claims, No Drawings

METHOD FOR TESTING SUBSTANCES ON BIOMATRICES

The present invention relates to a method for testing substances on biomatrices. The biomatrices represent tissue equivalents, or in other words cells on porous matrices based on biocompatible polymers or polymer mixtures. Further subject matter of the present invention is therefore the use of tissue equivalents for testing substances. Also described are a method for production of porous matrices as well as the matrices produced by this method, a special method for obtaining cells for inoculation of the matrices, and the production of the tissue equivalents.

Tissue engineering is an interdisciplinary field that combines engineering and materials sciences with medicine. The goal is to restore damaged tissue or to improve its function.

The principle of tissue engineering is conceptually simple: Firstly cells are prepared, for example by taking some cells from an organism and multiplying them in vitro. The multiplied cells can then be embedded in a framework substance, thus forming a complete, living tissue equivalent.

Of special importance for the functional capability of tissue equivalents are the nature and structure of the framework substance used, or the matrix as it is also referred to hereinafter. Aside from the material to be used, which usually comprises biodegradable polymers, the pore size, porosity and surface as well as the pore geometry, morphology of the pore wall and connectivity between the pores have important influences for further development of the cells embedded in the framework substance and ultimately for the three-dimensional structure of the tissue equivalents.

Methods for generating such biomatrices are already known. For example, techniques from the field of textiles have already been used to produce fibrous biomatrices with woven and fleece-like qualities. A further common method, in which salt crystals are first incorporated into the biodegradable polymer and subsequently dissolved out, makes it possible to control the pore size via the particle size and the porosity via the salt/polymer ratio (WO 98/44027). In a modification of the method, the biodegradable polymers dissolved in a solvent are applied onto what is known as a porogenic material, which is then dissolved out of the composite material once again, leaving behind pores with the geometry of the negative image of the said porogenic material (WO 01/87575 A2). Coated matrices also are already known (for example, see WO 99/09149 A1).

The test as to whether a certain substance is toxic for the human or nonhuman animal body is a critical step in the development of a drug for human or veterinary medicine. In principle, it is desirable to recognize potential toxicity as early as possible. It is not an uncommon situation that active ingredients have had to be taken off the market, because they were causing acute liver failure, or in other words exhibiting previously unknown liver toxicity.

In the past, the toxicological testing of pharmaceutically active substances, pesticides, food additives and further environmental substances has been undertaken either in vivo in experimental animals or by means of in vitro systems such as bacterial (for example, Ames test) and animal cell cultures. In the bacterial test systems and some of the animal cell cultures, however, metabolic activity is completely absent, and so toxic metabolic products cannot be detected with such systems. In order to compensate for this problem, it has been the practice in the past to use certain enzyme extracts, such as rat liver extracts. However, the metabolic activity simulated in this way is not necessarily consistent with that in the human or animal. Moreover, it may be that highly reactive metabolites do not reach their target molecules and so cannot be detected.

There has also been no lack of attempts to cultivate differentiated human cells having particular metabolic activities in vitro and in this way to achieve a test system that reasonably approximates the human metabolism. However, since differentiated cells can be cultivated only under limited conditions, among other reasons because the mechanical and/or enzymatic treatments that must necessarily be performed to isolate the cells lead to loss of and/or damage to the cell-to-cell contacts during formulation of cell cultures, certain measures were necessary to be able to establish a suitable cell culture at all. As an example, attempts have been made to immortalize liver cells, but this can lead to artifacts. Moreover, tissue normally dies within a very short time under culture conditions, since adequate exchange of nutrients and metabolic products is usually not ensured.

Thus the known in vitro systems suffer in particular from the disadvantage that they cannot simulate the complex metabolism of a human or animal organism. This means that the results obtained with these systems are even less transposable than the results of animal experiments. It may not be possible to determine sufficiently or at all the risk of administering the substances to be tested or of ingesting them, especially in the case of humans.

The object underlying the present invention is to provide a functional tissue equivalent with which the said tests on substances can be carried out satisfactorily. The invention achieves this by particular biomatrices, which can be obtained with a special method and which are used to construct a suitable tissue equivalent.

The subject matter of the present invention is therefore the method defined in the claims. It is an in vitro method.

The substances to be tested are substances with which humans or nonhuman animals, especially domestic or useful animals, are or could come into contact, especially those that are or could be ingested by humans or a nonhuman animal. Thus these substances include in particular active ingredients used in pharmaceuticals and plant protection, food additives and a plethora of environmental substances, with which humans or nonhuman animals could come into contact.

The inventive method is used in principle to investigate interactions of a substance to be tested with the tissue equivalent. In this connection, interaction is to be understood both as an action of the substance on the tissue equivalent and an action of the tissue equivalent on the substance.

For example, the inventive method can be used in particular to determine whether the tissue equivalent changes under the effect of the substance. A finding of this type usually includes examination of at least one condition (parameter) of the tissue equivalent or a part thereof comprising at least one cell. In principle, all observed or measured variables that describe a particular state of the tissue equivalent can be used as parameters. They include in particular cytological parameters, such as cell morphology, cell viability and cell division rate, biochemical parameters such as certain metabolic activities, for example the induction of certain enzymes, and the formation of certain metabolic products, as well as molecular biology parameters, such as the presence of certain nucleic acids and proteins.

Changes of cell morphology can be investigated visually, for example under the microscope. In particular, the cell size can be determined.

The viability of cells of the tissue equivalent can be determined in ways known in themselves, for example by means of known staining methods. The use Trypan Blue, Neutral Red or other chromogenic substrates such as 3-(4,5-dimethylthiazol-2-yl)-5-(3-carboxymethoxyphenyl)-2-(4-sulfophenyl)-2H-tetrazolium (live/dead stains) has long been known for this purpose to those skilled in the art. Also worthy of mention is electronic viability assay, such as by means of current exclusion methods (CASY® technology).

Certain enzyme activities, such as the enzymes participating in phase I and/or phase II biotransformations, can be biochemically determined in accustomed manner, for example by using substrates whose conversion leads to a detectable product that if at all possible is also quantifiable. Nucleic acids and proteins, such as enzymes, can be determined with the common molecular biology analysis methods.

For example, induction of a series of cytochromes P450 (such as 1A1, 1A2, 2A1, 3A4, 3A5, 2B6, 2C8, 2C9, 2C11, 2C19, 2D6, 2E1) can be determined by enzymatic or even molecular biology methods.

In accordance with this aspect, the inventive method is directed in particular at the testing of substances, in order to determine whether the test substance has a toxic effect on cells of the tissue equivalent (cytotoxicity). In this sense, those of the aforesaid parameters that can reproduce a cytotoxic effect are preferred.

As a rule, any change of the tissue equivalent can be observed in cells of the tissue equivalent. In certain cases, however, a change of the tissue equivalent can also be observed because of a change of the culture medium, for example if the tissue equivalent forms a metabolic product under the effect of the test substance and releases it into the surrounding culture medium.

In addition, it can also be determined with the inventive method whether the test substance experiences a change under the effect of the tissue equivalent. Such changes include in particular a change of the chemical structure of the test substance and the formation of adducts of the test substance with other substances made available by the tissue equivalent. The change of the test substance occurring under the effect of the tissue equivalent will be referred to here as a biotransformation, and the resulting products originating from the test substance will be referred to as metabolites. Such biotransformations include in particular phase I biotransformations, such as hydroxylation reactions, and phase I biotransformations, such as glucoronidation, sulfation, methylation, acetylation, amino acid conjugation and glutathione conjugation. The phase I biotransformations usually result in an increase in polarity of the test substance and/or in introduction of chemically reactive groups that can then participate in the phase II transformations.

In accordance with this aspect, the inventive method is directed in particular at the testing of substances in order to determine whether the test substance has been metabolized by the cells of the tissue equivalent (biotransformation).

The products participating in such biotransformations, or in other words especially the substance to be tested as starting material as well as the metabolites derived therefrom, can usually be determined with conventional analysis methods, wherein the culture medium and/or the cells of the tissue equivalent can be subjected to determination. In this connection there can be mentioned in particular chromatographic techniques, such as HPLC, spectrometric methods such as mass spectrometry, and immunological methods, with which the metabolites can be detected by means of suitable antibodies.

To perform the inventive method, the tissue equivalent is usually maintained in aqueous medium, in which nutrients are added and metabolic products are removed, and the necessary gas exchange is assured. For this purpose the medium usually contains the necessary nutrients. The relevant media for cultivation of human cells can be mentioned in this connection. As an example, normal William's medium E (supplemented with 10% fetal calf serum) has proved suitable for liver tissue equivalents, which are preferably used in the inventive method. Human sera or fractions thereof are also suitable.

In order to ensure adequate nutrient supply or sufficient gas exchange, the medium is usually agitated. Suitable devices in which inventive tissue equivalents can be cultivated have long been known to those skilled in the art and are found in particular in the field of bioreactors.

The test substance or substances is or are added to the medium, which usually already contains the tissue equivalent, at an appropriate point in time. It will be advisable to test various concentrations, starting with the lowest concentration. A plurality of test substances can be added to the medium as a mixture of substances or separately.

The decision as to whether the effect of the substance or substances has led to a change of the tissue equivalent and/or of the substance(s) usually requires at least two determinations of a condition (parameter), namely one determination before the effect and one determination after the effect. If the comparison of the results obtained with two determinations indicates a deviation, a change has occurred. In particular, it is possible to conduct more than two determinations of the same condition and/or determinations of several conditions. In this connection, it is advisable to provide a plurality of identical tissue equivalents in the same medium, so that one tissue equivalent can be sampled for each determination, without influencing the remaining tissue equivalents.

Hereinafter the tissue equivalents themselves as well as their underlying matrices and their production will be described.

The degree of porosity is the numerical value in % of the ratio of the pore volume to the total volume of the matrix.

Pores are to be understood as cavities present in the inventive matrix. In the present case they have a polygonal and especially octagonal shape when viewed in a two-dimension section or an angular geometry when viewed in three dimensions. Preferably the geometry is also characterized by extensions, whereby the geometry of the cavities can be compared with the form of nerve cells. The size of a pore can be indicated as a diameter, or in other words the mean of the longest and shortest diameters of the pores visible in the two-dimensional section.

The inventive matrix has pores with different sizes, and those sizes are distributed over a certain range (pore-size distribution). According to the invention, it is important that a matrix have a broad pore-size distribution, extending from pores with a size in the range of approximately 150 μm to pores with sizes in the range of approximately 300 μm or wider. In accordance with one aspect, therefore, an inventive matrix should have pores with a size of 150 μm or smaller. Matrices containing pores with a size of 140 μm or smaller are preferred. Particularly advantageous are matrices containing pores with a size of 130 μm or smaller. In accordance with a further aspect, an inventive matrix should contain pores with a size of 300 μm or larger. Matrices containing pores with a size of 350 μm or larger are preferred. Particularly advantageous are matrices containing pores with a size of 370 μm or larger. Matrices containing both pores with a size of 150, 140 or 130 μm or smaller and pores with a size of 300, 350, 370 μm or larger belong to the invention. These values can be combined as desired to define minimum ranges, over which the pore-size distribution should extend, the ranges of 150 to 300, 140 to 350 and 130 to 370 being particularly worthy of mention. It is particularly preferred when the respective pore-size distribution has frequency maxima outside the range of 150 to 300 µm, or in other words one frequency maximum above a pore size of 300 µm and another frequency maximum below a pore size of 150 µm.

A typical inventive matrix has the following pore-size distribution: approximately 0.5% to 6%, preferably approximately 1% to 5%, even more preferably approximately 2% to 4% and especially approximately 3% of pores with a mean diameter in the range of 70 to 100 µm, approximately 2% to 8%, preferably approximately 3% to 7%, even more preferably approximately 4% to 6% and especially approximately 5% of pores with a mean diameter in the range of 101 to 115 µm; approximately 2% to 8%, preferably approximately 3% to 7%, even more preferably approximately 4% to 6% and especially approximately 5% of pores with a mean diameter in the range of 116 to 130 µm; approximately 1% to 7%, preferably approximately 2% to 6%, even more preferably approximately 3% to 5% and especially approximately 4% of pores with a mean diameter in the range of 131 to 300 µm; approximately 11% to 23%, preferably approximately 13% to 21%, even more preferably approximately 15% to 19% and especially approximately 17% of pores with a mean diameter in the range of 301 to 330 µm; approximately 4% to 10%, preferably approximately 5% to 9%, even more preferably approximately 6% to 8% and especially approximately 7% of pores with a mean diameter in the range of 331 to 360 µm; approximately 5% to 17%, preferably approximately 7% to 15%, even more preferably approximately 9% to 13% and especially approximately 11% of pores with a mean diameter in the range of 361 to 390 µm; approximately 7% to 19%, preferably approximately 9% to 17%, even more preferably approximately 11% to 15% and especially approximately 13% of pores with a mean diameter in the range of 391 to 420 µm; approximately 3% to 9%, preferably approximately 4% to 8%, even more preferably approximately 5% to 7% and especially approximately 6% of pores with a mean diameter in the range of 421 to 450 µm; approximately 12% to 24%, preferably approximately 14% to 22%, even more preferably approximately 16% to 20% and especially approximately 18% of pores with a mean diameter in the range of 451 to 480 µm; and approximately 5% to 17%, preferably approximately 7% to 15%, even more preferably approximately 9% to 13% and especially approximately 11% of pores with a mean diameter in the range of 481 to 510 µm. Thus there is usually obtained a pore-size distribution with more than one maximum, which corresponds to an accumulation of pores in more than one size range. This is particularly important for the properties of inventive matrices.

The cavity volume and thus the degree of porosity can be determined in known ways by porosimetry.

As an example, the pore sizes and thus also the pore-size distribution can be determined by scanning electron microscopy. For this purpose, thin sections of the matrix to be investigated are prepared and coated with gold. The scanning electron micrographs are evaluated by measuring all pores within a defined area, specifically by determining the longest and shortest diameter for each pore, adding the two values and dividing the total by 2.

The term "matrix" also refers to a three-dimensional support suitable for colonization by cells. In this sense the matrix functions as a three-dimensional structural pattern (template) for colonization by cells or tissues. Such colonization preferably takes place in vitro.

In principle, the polymer can be any polymer usable in the discipline. This encompasses in particular biocompatible polymers, which permit colonization by living cells on the polymer. There can be used polymers that are substantially non-biodegradable or are at least predominantly biodegradable.

The expression "biodegradable" refers to a material that life forms (or bodily fluids or cell cultures derivable from life forms) are able to transform to metabolizable products. Examples of biodegradable polymers are bioabsorbable and/or bioerodable polymers. Bioerodable refers to the ability to be dissolved or suspended in biological fluids. Bioabsorbable means the ability to be taken up by cells, tissue or fluids of a life form.

Biodegradable polymers that are suitable according to the invention include in principle all polymers usable in the discipline, meaning not only the polymers already established in the field of tissue engineering but, for example, also polymers that have found uses in devices for release of active ingredients, such as bandages and active-ingredient implants.

Suitable natural polymers include, for example, polypeptides such as albumin, fibrinogen, collagen and gelatins, as well as polysaccharides such as chitin, chitosan, alginate and agarose. These natural polymers may even be modified under some circumstances. For example, proteins such as collagen can be cross-linked.

Examples of suitable synthetic polymers are certain polyanhydrides, especially poly(sebacic acid/hexadecane diacid), poly(ε-caprolactone), poly(ortho esters) and especially poly(α-hydroxy esters), such as poly(glycolic acid), poly(lactic acid) and poly(glycolic acid/lactic acid). Thus the inventive matrices and implants are preferably based on biodegradable polymers containing the repeating units of formula (I):

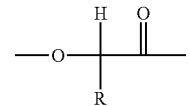

where $R^1$ stands for hydrogen or methyl. As regards the lactic acid units, the L-form (the S-enantiomer) is preferred. A particularly preferred polymer is poly(glycolic acid/lactic acid) with a glycolic acid to lactic acid ratio of 99:1 to 1:99, preferably 10:90 to 90:10, for example 15:85 mol %.

Mixtures of two or more polymers may also be expedient.

Besides the nature of the polymer, its molecular weight also influences the properties of the resulting matrix. In general, the porosity of the matrix decreases with increasing molecular weight of the polymer used. This is particularly true if the material is expanded during production, or in other words pressurized with a gas such as $CO_2$, which at first is dissolved in the polymer and then forms pores when the pressure is lowered.

Furthermore, the crystallinity of the polymer used affects the properties of the resulting matrix. In this connection, the porosity of the resulting matrix generally increases with decreasing crystallinity, and so amorphous polymers are preferred in particular for matrices with high porosity. This aspect also has particularly important influence when the material is expanded during production of the matrix.

The porous matrices based on a biocompatible polymer can also be characterized in that the surface of the matrix is coated with at least one extracellular matrix protein.

Extracellular matrix proteins are generally known. Preferred according to the invention are collagens, especially type I and IV collagens, laminin and fibronectin. These proteins can be produced in purified form in ways known in themselves, or can even be obtained commercially. According to one embodiment, coatings of inventive matrices contain fibronectin as the extracellular matrix protein. According to a further embodiment, coatings of inventive matrices contain a mixture of type I collagen, laminin and type IV collagen as the extracellular matrix protein. In this case, the mixture contains the proteins in approximately equal weight proportions.

According to the invention, particularly preferred are matrices that are coated in the manner described in the foregoing and that satisfy at least one of the following additional criteria:

The pores of the matrices have the pore sizes or pore-size distribution indicated hereinabove;
the degree of porosity is 93% to 98%;
the pores have the geometry indicated hereinabove;
the biocompatible polymer is one of the natural or synthetic polymers indicated hereinabove, especially poly(glycolic acid/lactic acid) with a lactic acid content of approximately 85 mol % and a glycolic acid content of approximately 15 mol %.

Such coated matrices can be obtained, for example, by dipping the uncoated matrix in a solution containing the protein or protein mixture intended for the coating and then drying the matrix wetted with the solution. Depending on the dimensions of the matrix body to be coated, the solution usually wets mainly the outer regions of the matrix body, whereas relatively little solution penetrates into the interior of the matrix body. The consequence of this can be that the entire matrix surface is not uniformly coated, but instead the coating density decreases from the exterior to the interior.

Alternatively or in addition to a coating, biologically active substances can be absorbed in the polymer or even cross-linked therewith. For this purpose there are used, for example, synthetic active ingredients (inorganic or organic molecules), proteins, polysaccharides and further sugars, lipids and nucleic acids, which influence cell growth, cell migration, cell division, cell differentiation and/or tissue growth, for example, or have therapeutic, prophylactic or diagnostic effects. Examples worthy of mention are vasoactive ingredients, neuroactive ingredients, hormones, growth factors, cytokines, steroids, anticoagulants, antiinflammatories, immuno-odulating active ingredients, cytotoxic active ingredients, antibiotics and antiviral active ingredients.

One method for production of a porous matrix on the basis of a biocompatible polymer or polymer mixture is characterized in that a mixture of polymer particles and salt particles with well defined particle size is compacted, after which the salt is dissolved out.

Polymer particles with a particle size in the range of approximately 20 to 950 µm, advantageously in the range of approximately 20 to 760 µm or approximately 50 to 760 µm and especially in the range of approximately 108 to 250 µm, and salt particles with a particle size in the range of approximately 90 to 670 µm, advantageously in the range of approximately 110 to 520 µm and especially in the range of approximately 250 to 425 µm have proved expedient for adjustment of the desired pore sizes or pore-size distribution. Furthermore, a weight ratio of polymer particles do salt particles in the range of 1:100 to 1:10, advantageously in the range of 1:50 to 1:15 and especially in the range of approximately 1:20 to 1:18 have proved expedient for adjustment of the desired porosity.

It has further proved expedient to use salt and polymer with a particular particle-size distribution. As regards the salt used for production of the matrix, it is favorable for the proportion of salt with a particle size of 250 µm to 320 µm to be approximately 15% to 50%, advantageously approximately 18% to 42% and preferably approximately 22% to 28%; for the proportion of salt with a particle size of 330 µm to 380 µm to be approximately 20% to 65%, advantageously approximately 30% to 52% and preferably approximately 42% to 46%; and for the proportion of salt with a particle size of 390 µm to 425 µm to be approximately 15% to 62%, advantageously approximately 25% to 42% and preferably approximately 29% to 33%, wherein the percentages relate to the total weight of salt used for production. Proportions with particle sizes above or below the indicated ranges are not excluded for this purpose.

According to a special embodiment, it has proved favorable for the proportion of salt particles with a particle size of 108 µm to 140 µm to be 1 to 15 wt %, preferably 4 to 12 wt % and especially 7 to 9 wt %; for the proportion of salt with a particle size of 145 µm to 180 µm to be 1 to 11 wt %, preferably 3 to 9 wt % and especially 5 to 7 wt %; for the proportion of salt with a particle size of 185 µm to 220 µm to be 3 to 21 wt %, preferably 7 to 17 wt % and especially 10 to 14 wt %; for the proportion of salt with a particle size of 225 µm to 250 µm to be 1 to 11 wt %, preferably 3 to 9 wt % and especially 5 to 7 wt %; for the proportion of salt with a particle size of 250 µm to 320 µm to be 15 to 50 wt %, preferably 18 to 42 wt % and especially 22 to 28 wt %; for the proportion of salt with a particle size of 330 µm to 380 µm to be 15 to 50 wt %, preferably 18 to 42 wt % and especially 22 to 28 wt %; and for the proportion of salt with a particle size of 390 µm to 425 µm to be 5 to 29 wt %, preferably 10 to 24 wt % and especially 15 to 19 wt %.

As regards the polymer used for production of the matrix, it is favorable for the proportion of polymer with a particle size of 108 µm to 140 µm to be approximately 5% to 50%, advantageously approximately 10% to 30% and preferably approximately 14% to 18%; for the proportion of polymer with a particle size of 145 µm to 180 µm to be approximately 10% to 55%, advantageously approximately 15% to 40% and preferably approximately 20% to 24%; for the proportion of polymer with a particle size of 185 µm to 220 µm to be approximately 18% to 88%, advantageously approximately 32% to 76% and preferably approximately 43% to 49%; and for the proportion of polymer with a particle size of 225 µm to 250 µm to be approximately 5% to 45%, advantageously approximately 10% to 28% and preferably approximately 14% to 18%, wherein the percentages relate to the total weight of polymer used for production.

In order to obtain salt or polymer particles of the desired pore-size distribution, it is usually advisable to subject commercially available products to size reduction first of all. This can be achieved in devices commonly used for the purpose, such as beaters or mills. However, the desired particle-size distribution is ultimately controlled by subsequent sieving by means of common analytical sieves.

Compacting is preferably performed by the action of compression. For this purpose the polymer/salt mixture can be compressed in a conventional hydraulic press with a ram pressure in the range of approximately 780 psi to 1450 psi, advantageously in the range of approximately 840 psi to 1230 psi and especially in the range of approximately 900 to 1100 psi. It has proved expedient to allow the pressure to act for approximately 10 s to 360 s, advantageously approximately 40 s to 180 s and especially approximately 50 s to 70 s at temperatures in the range of 18° C. to 25° C.

The salt is dissolved out, for example, with water or aqueous solutions. For this purpose the compacted mixture (matrix blank) can be water-treated for approximately 1 h to 80 h, advantageously approximately 12 h to 62 h and especially approximately 36 h to 60 h.

In addition, it is advantageous for the compacted mixture to be stored at first in a $CO_2$ atmosphere before dissolution of the salt. Thus the compacted mixture can be gas-treated, for example, at a $CO_2$ pressure in the range of approximately 140 psi to 1650 psi, advantageously in the range of approximately 360 psi to 1120 psi and especially in the range of approximately 800 psi to 900 psi, for which purpose times in the range of approximately 1 h to 180 h, advantageously in the range of approximately 3 h to 60 h and especially in the range of approximately 12 h to 36 h have proved expedient. Thereafter the pressure is lowered, during which the rate of pressure lowering influences the formation of pores. Although the use of $CO_2$ is preferred, other gases such as air, nitrogen, helium, neon, krypton, argon, xenon or oxygen may also be suitable.

Thereafter the water or the aqueous solution is removed in ways known in themselves for the purpose of drying. For example, the matrix can be placed on absorbent paper for this purpose.

In accordance with a preferred embodiment, a polymer solution is added to the mixture of polymer particles and salt particles, and the solvent is removed prior to compacting. In this case the polymer particles and polymer solution can be based on the same polymer. However, different polymers, especially with different biodegradability, can also be used. The use of polymer solution has the advantage that quasi support pillars are drawn into the matrix, thus allowing the mechanical characteristics of the matrix to be improved. In particular, such a matrix has less tendency to crumble.

The solvent used should dissolve the polymer, but not the salt. Thereby it is ensured that the porogenic properties of the salt are influenced not at all or not significantly. Acetone, ethyl acetate, methylene chloride, chloroform, hexafluoroisopropanol, chlorinated and fluorinated aliphatic and aromatic hydrocarbons, tetrahydrofuran, methyl ethyl ketone, diethyl ketone and mixtures thereof are suitable, for example, for dissolving the polymers cited hereinabove. For dissolving poly(glycolic acid), poly(lactic acid) or poly(glycolic acid/lactic acid), and with a view to medical use, chloroform in particular is suitable.

If the polymer solution and the mixture of polymer particles/salt particles are added together, there is first formed a stirrable slurry, which then rapidly solidifies as the solvent is removed. The concentrations of the polymer in the solution are expediently to be chosen such that, on the one hand, the polymer is completely dissolved and, on the other hand, the solvent can be rapidly removed without dissolving the polymer particles to an appreciable extent.

A weight ratio of polymer particles to dissolved polymer of 10:1 to 1:100, advantageously 2:1 to 1:25 and especially 1:1 to 1:10 has proved favorable.

As regards the weight ratio of polymer particles to salt particles, a relatively high weight ratio of up to 1:200, 1:500 or 1:1000 in favor of salt can be chosen in the scope of this embodiment, the weight ratio of total polymer to salt after as being greater than 1:100. In this way porosities greater than 98% can be established.

In the method described in the foregoing, the salt is used as porogenic material. By definition, there is meant a solid or at least semisolid material, which is first united with the matrix-forming polymer to obtain a mixture and then is removed from the mixture once again, thus forming cavities (pores). For this purpose it is expedient that the porogenic material be soluble in at least one solvent and substantially insoluble in at least one further solvent. A material is substantially insoluble in particular if its solubility under the processing conditions, which usually correspond to temperatures in the range of 18° C. to 25° C. and normal pressure, is less than 30 wt %, preferably less than 20 wt %, especially less than 10 wt % and, for example, less than 5, 4, 3, 2 and 1 wt %.

The structure and properties of the resulting matrix are determined substantially by the porogenic material used for production thereof. In this connection, not only the nature of the porogenic material but especially the particle-size distribution of the porogenic particles has an influence. In general, therefore, not only the pore size but also the connectivity, or in other words the network of intercommunicating cavities, increases with increasing particle size. This network, which is also known as macrostructure or macroporous structure, is to be distinguished from the pores that can be obtained by expansion, since these are usually closed and therefore form a structure designated as microstructure or microporous.

Accordingly, special matrices can be obtained by a method for production of a porous matrix based on a biocompatible polymer or polymer mixture, which method is characterized in that a mixture of polymer particles, particles of a porogenic material and a polymer solution are compacted and then the porogenic material is dissolved out.

This method is in principle not limited to the features described hereinabove. Thus the polymer can be chosen from among polyanhydrides, poly(ortho esters), poly(α-hydroxy esters), poly(ester amides), polyamides, poly(ester ethers), polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidones, polysiloxanes, polystyrenes, polyurethanes, derivatized celluloses, (meth)acrylic acid polymers and copolymers. The porogenic material is preferably chosen from among water-soluble salts, such as sodium chloride, potassium chloride, sodium fluoride, potassium fluoride, sodium iodide, potassium iodide, sodium nitrate, sodium sulfate, sodium citrate, sodium tartrate, sugars (such as sucrose, fructose, glucose) and mixtures thereof, although waxy substances such as paraffins, beeswax and similar substances can also be used. Polymer, porogenic material and the solvent used to form the solution are in principle to be matched to one another such that the solution contains polymer in dissolved form and polymer particles in solid form, while not substantially dissolving the porogenic material.

The matrices obtainable with the method described hereinabove are preferably used according to the invention.

For testing of substances, there are used according to the invention tissue equivalents that comprise at least one of the matrices described hereinabove and at least one cell. Depending on the intended use, these cells can be chosen in particular from among liver cells, pancreas cells, fat cells, intestinal cells, skin cells, vessel cells, nerve cells, muscle cells, thyroid cells and tooth root cells. Special embodiments of inventive tissue equivalents relate to liver cells and pancreas cells.

For testing of substances, there are preferably used according to the invention tissue equivalents that comprise at least one matrix based on a biocompatible polymer and cells of at least two cell types, wherein the cells of the first cell type are hepatocytes and the cells of the second cell type are Langerhan's islet cells.

Depending on intended use, in other words especially on the function to be performed, certain ratios of hepatocytes to Langerhan's islet cells are advantageous. Thus one embodiment of the invention relates to the use of tissue equivalents that exhibit the endocrine characteristics of an equivalent pancreas organ. For this purpose a ratio of hepatocytes to Langerhan's islet cells of approximately $10^6$:3000 has proved advantageous. A further embodiment of the invention relates to the use of tissue equivalents that simulate the metabolic functions of a liver. For this purpose a ratio of hepatocytes to Langerhan's islet cells of approximately $10^6$:3-200, advantageously of $10^6$:10-100, especially of $10^6$:20-80 and particularly preferably of approximately $10^6$:35-45 has proved expedient.

It must be remarked that such tissue equivalents usually contain not only hepatocytes and Langerhan's islet cells but also further cells, namely and especially liver and pancreas cells that are also collected during cell isolation.

The cells or cell mixtures to be used for colonization of inventive matrices can be obtained in ways known in themselves. Thus, for example, a suitable tissue such as a section of liver or pancreas can be excised from an individual and prepared appropriately for inoculation and in vitro culturing of the matrix. In this case it is important that the cells have the highest possible viability rate.

If liver cells are obtained from liver tissue, it is to be ensured that the liver cells can be surrounded by a strong layer of connective tissue. In order to be able to isolate the liver cells with the highest possible fraction of viable cells, solutions of certain composition are used according to the invention.

In particular, there can be used an aqueous composition A containing NaCl, KCl and HEPES and having a pH of approximately 7.4 for perfusion of both a liver or pancreas section. In particular, 1000 mL of this solution contains approximately 8.3 g of NaCl, 0.5 g of KCl and 2.38 g of HEPES. Perfusion is preferably carried out at a temperature of approximately 37° C. and a flowrate of approximately 30 mL/min. A few minutes, especially approximately 5 to 120 minutes, for example approximately 7 minutes, are adequate to perfuse the tissue section sufficiently at the aforesaid flowrate.

Alternatively, there can also be used an aqueous composition A' containing ethylene glycol tetraacetic acid (EGTA) for perfusion of a liver or pancreas section.

Furthermore, there can be used an aqueous composition B with a pH of approximately 7.3 to 7.4, preferably approximately 7.35, containing NaCl, KCl, HEPES, $CaCl_2$, collagenase and trypsin inhibitor, for perfusion of both a liver or pancreas section. Preferably, 1000 mL of this solution contains 8.3 g of NaCl, 0.5 g of KCl, 2.38 g of HEPES, 0.7 g of $CaCl_2.2H_2O$, 500 mg of collagenase H and 7.5 mg of trypsin inhibitor. In this case also, perfusion at approximately 37° C. and a flowrate of approximately 30 mL/min has proved expedient. A few minutes, especially approximately 5 to 10 minutes, for example approximately 6 to 7 minutes, are adequate to perfuse the tissue section sufficiently.

Alternatively, there can also be used an aqueous composition B' containing collagenase and hyaluronidase for perfusion of a liver or pancreas section. Preferably 1000 mL of the solution contains 5 to 10 U/mL collagenase and 5 to 10 U/mL hyaluronidase.

It is advantageous for the viability of the cells to be obtained if the tissue section is treated first with composition A and then with composition B. Alternatively, there can be used composition A' first and then composition B'.

Following perfusion, the tissue section can then be dissected and shaken carefully in a suitable medium such as William's medium E. If the resulting cell suspension still contains relatively large cell debris, this can be removed in ways known in themselves, for example by filtering the cell suspension through a nylon net (200 µm). The cells of the filtrate can then be carefully pelletized, for which purpose three minutes of centrifuging at 50 g of and 4° C. has proved advantageous.

The obtained cells are applied on the matrices in ways known in themselves. As a rule, the cells are applied as cell-containing solution on the matrix, and are then incubated—usually under cell culture conditions—until cells adhere to the matrix. If more than one cell type, such as hepatocytes and Langerhan's islet cells, are applied on a matrix, the different cell types can in principle be applied together or successively. In accordance with a particular embodiment, there are first applied Langerhan's islet cells and then hepatocytes. Each application is followed by incubation, until at least part of the cells adheres to the matrix.

Inventive matrices and tissue equivalents exhibit decisive advantages. Thus the internal dimensions of the matrices permit efficient colonization with cells. On the one hand the matrices are freely deformable, and on the other hand they offer adequate stability and rigidity. The inventive matrices can be produced without having to use physiologically hazardous solvents, such as formaldehyde, and so no special method is necessary for elimination of the solvents, and the risk of remaining residual amounts of these solvents does not exist.

Inventive tissue equivalents have diverse possible uses. Among these, in vitro uses are worthy of special mention. Further subject matter of the present invention is therefore the inventive tissue equivalents for use in vitro.

Special use in this area is based on the building of tissue (tissue engineering). In this case the inventive matrices act almost as a framework (scaffold), into which the cells migrate and/or to which they adhere.

For this purpose the matrices can be inoculated with the desired cells, for example in vitro, for example by adding a cell-containing solution and incubating until cells have adhered to the matrix. Such a matrix with cells adhering thereto (referred to here as tissue equivalents) can then be subjected to further process measures, such as further cultivation, if necessary under the action of active ingredients, for example for further expansion of the cells or for modulation of the properties thereof, and/or can be stored until use in appropriate manner, for example on ice or in a bioflow reactor under standard conditions. In the scope of this use, it is advantageous if the cells destined for testing of substances can first be isolated and also expanded if necessary in vitro. In particular, this makes it possible to apply, on a matrix, different cell types, such as the hepatocytes described hereinabove, together with Langerhan's islet cells.

The following examples are intended to illustrate the invention without restricting the scope thereof.

EXAMPLE 1

Production of the Matrix
a) Without Polymer Solution

Polymer pellets (Resomer® RG 858, obtainable from Boehringer Ingelheim), are frozen in liquid nitrogen and shredded while frozen (Däschle Co. beater machine; 12000 rpm for 2 minutes). The shredded polymer particles are sieved. Particles with a size of 108 µm to 250 µm are used for production of the matrix. In this connection, 16 wt % of the polymer used has a particle size of between 108 µm and 140 µm, 22 wt % of the polymer used has a particle size of between 145 µm and 180 µm, 46 wt % of the polymer used has a particle size of between 185 µm and 220 µm, and 16 wt % of the polymer used has a particle size of between 225 µm and 250 µm. Salt is sieved and salt particles with a particle size of 250 µm to 425 µm are used for production of the matrix. In this connection, 25 wt % of the salt used has a particle size of between 250 µm and 320 µm, 44 wt % of the salt used has a particle size of between 330 µm and 380 µm, and 31 wt % of the salt used has a particle size of between 390 µm and 425 µm. 760 mg of salt particles and 40 mg of polymer particles are mixed with one another. The mixture is introduced into a stamping mold and compressed with a hydraulic press at a ram pressure of 1000 psi for 1 minute. Thereafter the matrix blanks are placed on a Teflon tray and treated for 24 hours in a $CO_2$ atmosphere (850 psi). The blanks are then treated with water for 24 hours, in order to dissolve out the included salt particles. Finally, the matrixes are dried for 12 hours on absorbent paper.

The resulting polymer matrix has a porosity of 95±2% and a well defined pore size of 250 μm±120 μm, as determined by means of scanning electron microscope.

b) With Polymer Solution

Salt (analytical purity) is ground (Däschle Co. beater machine; 12000 rpm for 2 minutes) and then sieved, and salt particles with a particle size of 108 μm to 425 μm are used for production of the matrix. In this connection, 8 wt % of the salt used has a particle size of between 108 μm and 140 μm, 6 wt % of the salt used has a particle size of between 145 μm and 180 μm, 12 wt % of the salt used has a particle size of between 185 μm and 220 μm, 6 wt % of the salt used has a particle size of between 225 μm and 250 μm, 25 wt % of the salt used has a particle size of between 250 μm and 320 μm, 26 wt % of the salt used has a particle size of between 330 μm and 380 μm, and 17 wt % of the salt used has a particle size of between 390 μm and 425 μm. 96 g of salt particles are mixed with 1 g of the polymer particles described in Example 1 a) and then with 100 mL of a chloroform solution containing 4 g of the dissolved polymer. The mixture obtained in this way is heated to 45° C. to 65° C., whereby the chloroform evaporates within approximately 25 minutes. The remaining mixture of salt and polymer is then compressed with a hydraulic press at a ram pressure of 1000 psi for one minute and thereafter treated with water for 24 hours, in order to dissolve out the included salt particles. Thereafter the matrix is gas-treated as described in the foregoing and finally dried for 12 hours on absorbent paper.

The resulting polymer matrix has a porosity of 96%.

By mixing 98.5 g of salt particles with 0.5 g of polymer particles and adding the mixture to 100 mL of a chloroform solution containing 1 g of polymer, there is obtained a matrix with a porosity of 99%.

By mixing 99.2 g of salt particles with 0.1 g of polymer particles and adding the mixture to 100 mL of a chloroform solution containing approximately 0.9 g of polymer, there is obtained a matrix with a porosity of 99%.

EXAMPLE 2 a) Coating of the Matrix with Fibronectin

The matrix from Example 1 is dipped into a carbonate buffer solution containing 3 μg/mL fibronectin from human plasma (Sigma) and having a pH of 9.4. After approximately 60 s, the matrix is removed from the solution, lyophilized and gamma-sterilized.

EXAMPLE 3

Cell Isolation

A liver section of a human donor is first perfused for 7 minutes at a flowrate of 30 mL/min and 37° C. with a solution (8.3 g of NaCl; 0.5 g of KCl; 2.38 g of HEPES; made up to 1000 mL with distilled water, pH 7.4). Thereafter the liver section is perfused for a further 6 to 7 minutes at a flowrate of 30 mL/min and 37° C. with a collagenase-trypsin inhibitor solution (8.3 g of NaCl; 0.5 g of KCl; 2.38 g of HEPES; 0.7 g of $CaCl_2.2H_2O$; 500 mg of collagenase (collagenase H, Boehringer Mannheim, Mannheim, Germany); 7.5 mg of trypsin inhibitor (ICN, Eschwege, Germany); made up to 1000 mL with distilled water; pH 7.35). After the end of perfusion, the liver section is dissected and shaken carefully in William's medium E. The cell suspension is filtered (nylon net; 200 μm) and then washed with William's medium E. Thereafter the cells are centrifuged for 3 minutes at 50 g and 4° C. The viability of the cells as determined with Trypan Blue is 95%.

Langerhan's islet cells are isolated in the same way from a pancreas section.

EXAMPLE 4

Cell Colonization

In the first step, the matrices coated in Example 2 are incubated with Langerhan's islet cells isolated according to Example 3.

For this purpose, 3000 islet cells per mL are suspended in a solution mixture of M199 and FKS (volume ratio of 19:1). The cell count is determined by counting under an inverse Olympus microscope in a 0.25 mm counting tube. Then 8 to 10 mL of this solution is applied with a pipette onto the matrix. The excess solution that does not remain in the matrix is discarded. The matrix treated in this way is then placed in the cell culture incubator for 4 hours to achieve adhesion of the cells. Thereafter a solution of William's medium E containing an unpurified liver cell suspension of approximately $5.0 \times 10^7$ viable hepatocytes and approximately $1.0 \times 10^6$ non-parenchymatous liver cells per mL is applied on the matrix. A pipette is used to apply 8 mL to 12 mL of solution; the excess solution not absorbed by the matrix is discarded.

EXAMPLE 5

Induction of Cytochrome P450 by Benzene

A tissue equivalent obtained according to Example 4 (approximately 124 mm×45 mm×5 mm) is cut into 8 strips. The strips are placed in approximately 1 liter of William's medium E, which is agitated. Adequate gas exchange is ensured, and the temperature of the medium is maintained at 37° C.

After the system has equilibrated, a first strip of tissue equivalent is removed and the CYP2E1 activity thereon is determined via the EFCOD test method. Using the said method, the CYP2E1 mediated O-dealkylation of 7-ethoxy-4-trifluoromethylcoumarin to 7-hydroxy-4-trifluoromethylcoumarin is determined.

Thereafter sufficient benzene is added to the medium to bring the benzene concentration to 0.005 mM. The benzene is allowed to act for several hours, while maintaining the medium in agitation and ensuring the gas exchange. Then the CYP2E1 activity is determined once again in the way described in the foregoing.

Thereafter the benzene concentration is raised to 0.01, 0.02, 0.05 and 0.1 mM, and the CYP2E1 activity is determined after the action of each benzene concentration.

Comparison of the CYP2E1 activities measured in this way reveals a distinct increase of the basic activity with increasing benzene concentration. Such a change reflects the known liver toxicity of benzene.

The invention claimed is:
1. A method for testing one or more substances, comprising cultivating a tissue equivalent,
allowing at least one substance to act on the tissue equivalent, and
determining whether the action of the substance has led to a change of the tissue equivalent, wherein the tissue equivalent comprises at least one tissue cell and a porous matrix based on a biocompatible polymer or polymer mixture, wherein the matrix possesses pores having frequency maxima above and below the range of 150 to 300 μm and the degree of porosity is 93 to 98%, wherein the matrix comprises approximately 1% to 7% of pores with a mean diameter in the range of 131 to 300 μm, and the matrix is obtainable by compacting a mixture of polymer particles and salt and then dissolving out the salt.

2. The method according to claim 1, wherein the matrix comprises approximately 2% to 6% of pores with a mean diameter in the range of 131 to 300 μm.

3. The method according to claim 1, wherein the matrix comprises approximately 3% to 5% of pores with a mean diameter in the range of 131 to 300 μm.

4. The method according to claim 1, wherein the matrix comprises approximately 4% of pores with a mean diameter in the range of 131 to 300 μm.

5. The method according to claim 1, wherein the biocompatible polymer is a biodegradable polymer selected from the group consisting of natural polymers and synthetic polymers.

6. The method according to claim 5, wherein the biodegradable polymer is poly(glycolic acid/lactic acid) with a lactic acid content of approximately 85 mol % and a glycolic acid content of approximately 15 mol %.

7. The method according to claim 1, wherein the surface of the matrix is coated with at least one extracellular matrix protein which is selected from the group consisting of collagens, laminin, and fibronectin.

8. The method according to claim 7, wherein the coating comprises a mixture of type I collagen, laminin, and type IV collagen.

9. The method according to claim 1, wherein the porous matrix based on a biocompatible polymer or polymer mixture can be obtained by compacting a mixture of polymer particles with a particle size in the range of approximately 20 to 950 μm, and sodium chloride particles with a particle size in the range of approximately 90 to 670 μm, and then dissolving out the sodium chloride.

10. The method according to claim 9, wherein the mixture of sodium chloride particles is composed of 15% to 50 wt % of particles with a particle size of 250 μm to 320 μm, 20% to 65 wt % of particles with a particle size of 330 μm to 380 μm, and 15% to 62 wt % of particles with a particle size of 390 μm to 425 μm.

11. The method according to claim 9, wherein the mixture of sodium chloride particles is composed of 1 to 15 wt % of particles with a particle size of 108 μm to 140 μm, 1 to 11 wt % of particles with a particle size of 145 μm to 180 μm, 3 to 21 wt % of particles with a particle size of 185 μm to 220 μm, 1 to 11 wt % of particles with a particle size of 225 μm to 250 μm, 15 to 50 wt % of particles with a particle size of 250 μm to 320 μm, 15 to 50 wt % of particles with a particle size of 330 μm to 380 μm, and 5 to 29 wt % of particles with a particle size of 390 μm to 425 μm.

12. The method according to claim 9, wherein the mixture of polymer particles is composed of 5 to 50 wt % of particles with a particle size of 108 μm to 140 μm, 10 to 55 wt % of particles with a particle size of 145 μm to 180 μm, 18 to 88 wt % of particles with a particle size of 185 μm to 220 μm, and 5 to 45 wt % of particles with a particle size of 225 μm to 250 μm.

13. The method according to claim 9, wherein the weight ratio of polymer particles to sodium chloride particles is 1:100 to 1:10.

14. The method according to claim 9, wherein a polymer solution is added to the mixture of polymer particles and sodium chloride particles and the solvent is evaporated before compaction.

15. The method according to claim 14, wherein the solvent dissolves the polymer but not the salt.

16. The method according to claim 15, wherein the solvent is selected from the group consisting of acetone, ethyl acetate, methylene chloride, chloroform, hexafluoroisopropanol, chlorinated and fluorinated aliphatic and aromatic hydrocarbons, tetrahydrofuran, methyl ethyl ketone, diethyl ketone, and mixtures thereof.

17. The method according to claim 15, wherein the polymer is poly(glycolic acid), poly(lactic acid) or poly(glycolic acid/lactic acid), and the solvent is chloroform.

18. The method according to claim 14, wherein the weight ratio of polymer particles to dissolved polymer is 10:1 to 1:100.

19. The method according to claim 9, wherein compaction is achieved by the action of pressure.

20. The method according to claim 9, wherein water is allowed to act on the compacted mixture in order to dissolve out the sodium chloride.

21. The method according to claim 20, wherein the water is removed.

22. The method according to claim 9, wherein the compacted mixture is first stored in a $CO_2$ atmosphere and then the sodium chloride is dissolved out.

23. The method according to claim 1, wherein the tissue equivalent comprises tissue cells of at least two cell types, wherein the cells of the first cell type are hepatocytes and the cells of the second cell type are Langerhans islet cells.

24. The method according to claim 23, wherein the ratio of hepatocytes to Langerhans islet cells is approximately $10^6$:3000.

25. The method according to claim 23, wherein the ratio of hepatocytes to Langerhans islet cells is approximately $10^6$:3-200.

* * * * *